US005725841A

United States Patent [19]

Duan et al.

[11] Patent Number: 5,725,841
[45] Date of Patent: Mar. 10, 1998

[54] AEROSOL FORMULATION CONTAINING AN ESTER-, AMIDE-, OR MERCAPTOESTER-DERIVED DISPERSING AID

[75] Inventors: Daniel C. Duan, St. Paul; James S. Stefely, Woodbury; David W. Schultz, Pine Springs; Chester L. Leach, Lake Elmo, all of Minn.

[73] Assignee: Minnesota Mining and Manufacturing Company, St. Paul, Minn.

[21] Appl. No.: 738,519

[22] Filed: Oct. 28, 1996

Related U.S. Application Data

[63] Continuation of Ser. No. 213,555, Mar. 16, 1994, Pat. No. 5,569,450, which is a continuation-in-part of Ser. No. 32,146, Mar. 17, 1993, abandoned.

[51] Int. Cl.$^6$ .............................. A61L 9/04; A61K 31/74; C08G 63/02; C08G 63/66

[52] U.S. Cl. .......................... 424/45; 424/78.17; 424/434; 424/435; 528/272; 528/300; 528/301; 528/302

[58] Field of Search .................................... 424/45, 78.17, 424/434, 435; 528/272, 300, 301, 302

[56] References Cited

U.S. PATENT DOCUMENTS

| | | | |
|---|---|---|---|
| 2,362,511 | 11/1944 | Teeters | 260/78 |
| 2,733,252 | 1/1956 | Thompson et al. | 260/410.9 |
| 2,789,992 | 4/1957 | Thompson et al. | 260/410.9 |
| 3,098,795 | 7/1963 | Kreps | 167/90 |
| 3,728,447 | 4/1973 | Osipow et al. | 424/70 |
| 3,933,825 | 1/1976 | Fiscella et al. | 260/268 R |
| 4,029,606 | 6/1977 | Isa et al. | 252/529 |
| 4,846,991 | 7/1989 | Suzue et al. | 252/89.1 |
| 4,948,583 | 8/1990 | Grollier et al. | 424/195.1 |
| 5,008,028 | 4/1991 | Jolley et al. | 252/68 |
| 5,126,123 | 6/1992 | Johnson | 424/45 |
| 5,250,293 | 10/1993 | Gleich | 424/78.04 |
| 5,300,255 | 4/1994 | Campbell et al. | 252/351 |
| 5,536,445 | 7/1996 | Campbell et al. | 252/308 |

FOREIGN PATENT DOCUMENTS

| | | |
|---|---|---|
| 521455 A2 | 1/1993 | European Pat. Off. . |
| 534731 A1 | 3/1993 | European Pat. Off. . |
| 666406 A5 | 7/1988 | Switzerland . |
| 91/04011 | 4/1991 | WIPO . |
| 91/14422 | 10/1991 | WIPO . |
| 92/00061 | 1/1992 | WIPO . |
| 92/00062 | 1/1992 | WIPO . |

OTHER PUBLICATIONS

*Polymer Preprints*, Japan (English Edition), vol. 41, No. 5–11, p. 1681.
JP 04169554 A (Derwent Abstract).
JP 04198394 A (Derwent Abstract).
Chemical Abstracts 117(14):134300a (Fujii, Mar. 1992).
Chemical Abstracts 117(14):134337h (Nakahara, Mar. 1992).
Chemical Abstracts 117(14):134340d (Tanaka, Mar. 1992).
Chemical Abstracts 117(24):237045r (Nakahara, May 1992).
Chemical Abstracts 117(24):237046s(Nakahara, May 1992).
Chemical Abstracts 117(26):254711x (Fujii, Jun. 1992).
Chemical Abstracts 118(4):24870q (Fujii, Jun. 1992).
Chemical Abstracts 118(8):62799f (Lache, 1991).
Chemical Abstracts 118(12):106175f (Nakahara, Nov. 1992).

*Primary Examiner*—Carlos A. Azpuru
*Attorney, Agent, or Firm*—Gary L. Griswold; Walter N. Kirn; Ted K. Ringsred

[57] ABSTRACT

A medicinal aerosol formulation containing a particulate drug and a dispersing aid derived from a hydroxyacid, a mercapto acid, or an amino acid.

19 Claims, No Drawings

AEROSOL FORMULATION CONTAINING AN ESTER-, AMIDE-, OR MERCAPTOESTER-DERIVED DISPERSING AID

CROSS-REFERENCE TO RELATED APPLICATION

This a continuation of application Ser. No. 08/213,555 filed Mar. 16, 1994, now U.S. Pat. No. 5,569,450, which is a CIP of application Ser. No. 08/032,146, filed Mar. 17, 1993 now abandoned.

BACKGROUND OF THE INVENTION

1. Field of the Invention

This invention relates to aerosol drug formulations. This invention also relates to dispersing aids for use in aerosol drug formulations. In another aspect this invention relates to aerosol formulations comprising hydrofluorocarbon propellants.

2. Description of the Related Art

Delivery of drugs to the lung by way of inhalation is an important means of treating a variety of conditions, including such common conditions as bronchial asthma and chronic obstructive pulmonary disease. Steroids, β-2 agonists, and anti-cholinergic agents are among the drugs that are administered to the lung for such purposes. Such drugs are commonly administered to the lung in the form of an aerosol of particles of respirable size (less than about 10 μm in diameter). In order to assure proper particle size in the aerosol, particles can be prepared in respirable size and then incorporated into a suspension formulation containing a propellant. Alternatively, formulations can be prepared in solution form in order to avoid the concern for proper particle size in the formulation. Solution formulations must nevertheless be dispensed in a manner that produces particles or droplets of respirable size.

Once prepared an aerosol formulation is filled into an aerosol canister equipped with a metered dose valve. In the hands of a patient the formulation is dispensed via an actuator adapted to direct the dose from the valve to the patient.

It is important that an aerosol formulation be stable such that the dose discharged from the metered dose valve is reproducible. Rapid creaming, settling, or flocculation after agitation are common sources of dose irreproducibility in suspension formulations. Sticking of the valve also can cause dose irreproducibility. In order to overcome these problems aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents have been used to overcome this problem. An alternative approach that avoids use of cosolvents involves materials that are soluble in hydrofluorocarbon propellants and are said to be effective surfactants or dispersing aids in an aerosol formulation. Among such materials are certain fluorinated surfactants and certain polyethoxy surfactants.

The materials used in medicinal aerosol formulations are taken into the lungs. It is therefore desirable that they be non-toxic or suitably metabolized or eliminated.

SUMMARY OF THE INVENTION

This invention provides a medicinal aerosol formulation, comprising:

(i) a dispersing aid comprising a compound comprising a chain of units derived from a precursor selected from the group consisting of a hydroxyacid, an amino acid, a mercapto acid, and a combination of any two or more of the foregoing;

(ii) a propellant; and (iii) a therapeutically effective amount of a particulate drug;

wherein the formulation is substantially readily redispersible and upon redispersion does not flocculate, cream, or settle so quickly as to prevent reproducible dosing of the drug.

The chain is optionally capped at one end or both. ends by a group that contains no hydrogen atoms capable of hydrogen bonding. The chain is also optionally bonded at one end or both ends to a moiety that contains an ionic group or a group that contains one or more hydrogen atoms capable of hydrogen bonding (e.g., an acid functional group such as an α-amino acid residue).

In another embodiment the dispersing aid comprises a compound comprising a chain of units of the general formula wherein each $R_1$ is an independently selected organic moiety that links the —X— group to the carbonyl group, and each X is independently —O—, —S—, or catenary nitrogen.

DETAILED DESCRIPTION OF THE INVENTION

This invention involves suspension aerosol formulations comprising a dispersing aid. The dispersing aid comprises one or more compounds. The compounds in the dispersing aid comprise at least one chain. The chain can be linear, branched, or cyclic. The compounds also optionally further comprise one or more of: an ionic group; a group that contains one or more hydrogen atoms capable of hydrogen bonding; or a group containing no hydrogen atoms capable of hydrogen bonding.

The chain comprises units derived from a hydroxyacid, amino acid, or mercapto acid. The chains can be homopolymer chains (i.e., those derived from a single such acid) or copolymer chains (e.g., chains containing randomly distributed units or blocks of units derived from any two or more such acids). As the terminology is used herein, a chain "derived from" a particular precursor need not be prepared from the precursor; rather this terminology is used to designate chains having a structure that could formally be obtained by condensation of the precursor.

A precursor hydroxyacid can be any hydroxyacid, e.g., a hydroxycarboxylic acid, or the corresponding lactone or cyclic carbonate, if any. It is preferred that the hydroxyacid be endogenous to the human body. Suitable hydroxycarboxylic acids include straight chain $C_2$–$C_6$ hydroxyalkyl carboxylic acids such as hydroxyacetic acid, hydroxypropionic acids (e.g., 2- or 3-hydroxypropionic acid), hydroxybutyric acids (e.g., 2-, 3-, or 4-hydroxybutyric acid), hydroxyvaleric acids (e.g., 2-, 3- 4-, or 5-hydroxyvaleric acid), hydroxycaproic acids (e.g., 2-, 3-, 4-, 5-, or 6-hydroxycaproic acid), branched chain $C_3$–$C_6$ hydroxyalkyl carboxylic acids (e.g., 2-hydroxydimethylacetic acid), malic acid monoesters, and the like. Suitable lactones include lactides, 1,4-dioxanone, valerolactone, and caprolactone. Suitable cyclic carbonates include trimethylene carbonate. Units derived from a hydroxycarboxylic acid can be designated by the general formula

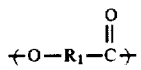

wherein $R_1$ designates an organic moiety that functions to link the heteroatom terminus (in this case —O—) to the carbonyl terminus

$R_1$ is preferably straight chain, branched chain, or cyclic alkylene or alkenylene, preferably containing from one to about six carbon atoms. When $R_1$ is alkylene or alkenylene it can also contain heteroatomic functional groups such as carbonyl, oxy, thio, or catenary nitrogen, preferably fully substituted catenary nitrogen wherein the substituent is free of hydrogen-donor hydrogen bonding functional groups. $R_1$ preferably contains one to about four catenary atoms. $R_1$ can also be arylene (e.g., 1,4-phenylene) or arylene substituted by functional groups that do not contain hydrogen atoms capable of hydrogen bonding, e.g., lower alkyl or lower alkoxy. The term "lower" when used in connection with alkyl, alkenyl, alkoxy, alkenylene, or alkylene groups refers to such groups having one to about four carbon atoms. $R_1$ can also be a combination of such arylene, alkenylene, and alkylene groups, such as 1,4-xylylene.

A precursor amino acid can be any compound having an amino group, preferably a secondary amino group, at least one carbon atom removed from an acid group such as a carboxylic acid group. Exemplary amino acids include secondary amino acids (sometimes referred to as "imino acids") such as sarcosine and proline. As with the hydroxyacids discussed above it is preferred that the aminocarboxylic acid be endogenous to the human body.

A unit derived from an amino acid can be designated by the general formula

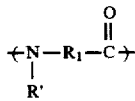

wherein $R_1$ is as defined above and R' is hydrogen or a group other than hydrogen, preferably a group that is free of hydrogen-donor hydrogen bonding functional groups. Exemplary suitable groups that can be bonded to the imino nitrogen include alkyl, alkoxyalkyl, haloalkyl, phenylalkyl, alkenyl, haloalkenyl, phenyl, alkylphenyl, alkoxyphenyl, halophenyl, and others readily selected by those skilled in the art. Preferably the alkyl, alkoxy, or alkenyl moieties in these functional groups contain from one to about eighteen, more preferably from one to about six carbon atoms. Most preferably they are lower alkyl, alkoxy, or alkenyl groups.

A precursor mercapto acid can be any compound comprising a thiol group and an acid group such as a carboxylic acid group. Exemplary mercapto acids include 2-mercaptopropionic acid, 3-mercaptopropionic acid, and mercaptoacetic acid. A unit derived from a mercaptocarboxylic acid can be designated by the general formula

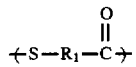

wherein $R_1$ is as defined above.

One skilled in the art can select units for inclusion in the chains of the compounds of the dispersing aid described above with due consideration of factors that affect dispersing aid function or suitability for inhalation, such as possible ease of metabolism, solubility, crystallinity, structural homogeneity, molecular weight, degree of branching, relative amount of polar and non-polar portions of the chain, the particular propellant to be used in connection with the dispersing aid, and the particular drug to be formulated. For example, certain homopolymer chains or chains having excess aromatic content can be excessively crystalline and unsuitable for use with HFC propellants. The use of minor amounts (e.g., 10 to 40 mole percent) of "comonomers" or the use of an enantiomeric mixture of a chiral monomer can serve to render a material more amorphous. Likewise, excessive hydrogen bonding can interfere with dispersing aid function but is readily avoided by selecting appropriate chain components.

The term "chain length" as used herein (sometimes referred to as "n" in connection with the several formulae appearing herein) denotes the average number of monomer units in the chain. Generally chains contain a plurality of the above-described units. Chain length is generally less than 100, preferably between about 3 and about 70, and more preferably between about 3 and about 40, and most preferably between about 3 and about 14. Particularly preferred chain length will depend on certain of the factors discussed above. Relatively short chain lengths (e.g., from six to twelve units) are preferred inasmuch as these shorter chains could be expected to be more readily metabolized than materials having greater chain lengths. Also it has been found that with lactic acid based dispersing aids chain lengths of about four or more are particularly preferred for use with HFC-227, while chain lengths of about six or more are particularly preferred for use with HFC-134a.

It is well known that polymers and/or oligomers contain a distribution of chain lengths. In dispersing aids for use in the invention it is preferred to remove components having a chain length of less than three (removal of such short chain length components will of course raise the average chain length "n" of a given dispersing aid composition). In those dispersing aids where excessive crystallinity is problematic it is often helpful to remove the higher molecular weight fraction from the dispersing aid composition.

The compound contains at least one chain as described above. In certain embodiments the compound contains two or more such chains arranged, e.g., as described below in connection with divalent and polyvalent capping groups.

A chain can be capped at one end or both ends by a monovalent, divalent or polyvalent organic moiety (each valence of the capping group being independently bonded to a chain) that does not contain hydrogen atoms capable of hydrogen bonding. Such groups are well known and can be readily selected by those skilled in the art. Those skilled in the art will understand that the particular structure of such a group is to a degree, determined by factors relating to synthetic expediency (as discussed below in connection with preparation of the dispersing aid) such as, for example, whether a carbonyl terminus or a heteroatom terminus of a chain is capped by a particular group. Preferred monovalent organic moieties for capping the heteroatom terminus of a chain include organocarbonyl groups such as those of the formula

wherein $R_2$ is straight chain, branched chain, or cyclic alkyl optionally containing heteroatomic functional groups such as carbonyl, oxy, thio, or catenary nitrogen, preferably containing from one to about eighteen carbon atoms, and more preferably containing one to about six carbon atoms, phenyl, or phenyl substituted by one or more lower alkyl, lower alkoxy, or halogen groups. Groups of the formula —$R_2$ are also suitable. Other suitable monovalent organic moieties, particularly for capping the carbonyl terminus of a chain, include those of the formula —$OR_2$, —$SR_2$, or —$N(R_2)_2$ wherein $R_2$ is as defined above.

In embodiments that comprise two or more chains the groups that cap the chains (the capping groups) can be identical to or different from one another. Furthermore in such embodiments the capping groups need not terminate the compound; rather they can be divalent or polyvalent groups that bridge two or more chains. Exemplary bridging groups (which are a subgenus of capping groups) include straight chain, branched chain, or cyclic alkylene groups optionally containing heteroatomic functional groups such as carbonyl, oxy, thio, or catenary nitrogen. Groups derived from dihydridic alcohols such as polyethylene glycol [i.e., groups of the formula $-(OCH_2CH_2)_nO$ or $-(OCH_2CH_2)_n$ wherein n is an integer greater than one], polypropylene glycol [i.e., groups of the formula $-(OCH(CH_3)CH_2)_nO$ or $-(OCH(CH_3)CH_2)_n$ wherein n is an integer greater than one] are suitable. Also suitable are groups derived from polyhydric alcohols, such as 1,2,3-trioxypropane (derived from glycerol) and polyvalent groups such as

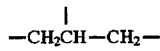

and the like. Bridging groups for bridging between heteroatom termini include those of the formula

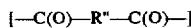

wherein R" is straight chain, branched chain, or cyclic alkylene or alkenylene optionally containing heteroatomic functional groups such as carbonyl, catenary nitrogen, oxy, or thio, and preferably containing from one to about eighteen carbon atoms, phenylene, or phenylene substituted by one or more lower alkyl, lower alkoxy, or halogen groups.

The chain is also preferably bonded at one end or both ends to a moiety that contains an ionic group or a group that contains hydrogen atoms capable of hydrogen bonding. Such groups are well known and can be readily selected by those skilled in the art. Suitable ionic groups include quaternary ammonium groups, sulfonate salts, carboxylate salts, and the like. Hydrogen, when bonded to the heteroatom terminus of a chain, is capable of hydrogen bonding. Other suitable groups that contain hydrogen atoms capable of hydrogen bonding include acid functional groups, amides, carbamates, and groups such as amino, hydroxyl, thiol, aminoalkyl, alkylamino, hydroxyalkyl, hydroxyalkylamino, sugar residues, and the like. The suitability of any particular group for use in connection with a particular chain will of course be dependent upon the structure of the respective group and chain. Those skilled in the art can readily select suitable combinations with due consideration of factors known to affect functional group compatibility. For example, in the instance of a hydroxycarboxylic acid-derived chain, primary or secondary amino groups are preferably protonated in order to avoid nucleophilic displacement within the chain by an amino group.

Suitable acid functional groups include carboxylic acid, which is an inherent feature of the dispersing aids prepared according to step (i) or step (ii) of the Reaction Scheme discussed in detail below. Other preferred moieties that contain acid functional groups include α-amino acid residues or esters thereof. In one such embodiment the amino group of the α-amino acid is bonded to a carbonyl terminus of the chain. In such embodiments preferred α-amino acid residues include those of the formula

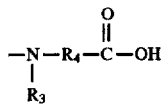

wherein $R_3$ is hydrogen and $R_4$ is straight chain, branched chain, or cyclic alkylene containing one catenary carbon atom and a total of one to about 12 carbon atoms, optionally substituted by one or more of lower alkoxy, lower alkylthio, carboxy, mercapto, hydroxy, phenyl, hydroxyphenyl, indolyl, guanidinyl, carbamido (i.e., —$NHC(O)NH_2$), imidazolyl, or acylamino (i.e., —$C(O)NH_2$), or wherein $R_3$ and $R_4$ together form a straight chain butane-1,1,4-triyl group optionally substituted by hydroxy. In embodiments wherein the amino acid residue contains a nucleophilic group such as hydroxy or mercapto, the amino group can be blocked, e.g., by an acetyl group, and the carbonyl terminus of a chain can be bonded to the amino acid residue via the nucleophilic —S— or —O— atom of the amino acid.

In another embodiment the α-amino acid residue is bonded to the heteroatom terminus (e.g., to an —O—, —S—, or —NR'— group) of the chain and is of the formula

wherein $R_4$ is as defined above and $R_5$ is hydrogen or a blocking group such as organocarbonyl (e.g., acetyl) as defined above.

Most preferred amino acid residues are those that are derived from endogenous amino acids or esters thereof such as glycine, alanine, valine, leucine, isoleucine, serine, threonine, phenylalanine, tyrosine, tryptophan, cysteine, methionine, aspartic acid, glutamic acid, asparagine, glutamine, lysine, hydroxylysine, arginine, citrulline, histidine, proline, and hydroxyproline. Taurine, a β-amino sulfonic acid, is also suitable.

As with the above-described capping groups, the moiety containing an ionic or hydrogen bonding group need not terminate the compound; rather it can be a divalent or polyvalent group bridging the chains. Exemplary groups of this type include alkylene diimino groups and polyoxyalkylenediimino groups.

It is preferred (but as described below in connection with preparation of a formulation of the invention, not necessary) that the dispersing aid is soluble in a propellant composition comprising a hydrofluorocarbon, such as HFC-134a (1,1,1, 2-tetrafluoroethane) or HFC-227 (1,1,1,2,3,3,3-heptafluoropropane) in an amount effective to stabilize a suspension aerosol formulation. The amount that constitutes such an effective amount will be dependent upon certain factors, including the particular dispersing aid (e.g., the hydroxyacid from which the chain is derived, the chain length, the presence or absence of terminal and capping groups), the particular propellant, the particular drug in the formulation, and the physical form of the drug (e.g., the particle size of the drug). Such effective amounts can be readily determined by those skilled in the art with due consideration of the factors discussed above.

Particular preferred embodiments of the dispersing aid include those wherein the chain comprises units derived from lactic acid, glycolic acid, trimethylene carbonate, polyhydroxybutyrate, or p-dioxanone. Lactic acid is preferred. In embodiments where the lactic acid unit is the only component of the chain, the chain is preferably from about 3 to about 40 units long. Lower chain lengths (e.g., from six to twelve) are more preferred inasmuch as the chains could be expected to be more readily metabolized than longer chain length materials. Also in such embodiments it is preferred that the chain be capped at one end as described above, preferably by an organocarbonyl group, and most preferably by an acetyl group.

A further preferred embodiment comprises units derived from glycolic acid (i.e., units of the formula —$OCH_2C(O)$—) and units derived from lactic acid. In such embodiments the chain preferably contains a total of 3 to about 40 units. Also in such embodiments it is sometimes preferred that the chain be capped at one end as described above, preferably by an organocarbonyl group, and most preferably by an acetyl group.

A medicinal aerosol formulation of the invention comprises a dispersing aid as described above. A single dispersing aid, for example a substantially monodisperse material, can be used. Also a combination of one or more dispersing aids can be used, e.g., two dispersing aids comprising the same constituent monomers but having different chain lengths can be used to provide a formulation comprising a dispersing aid having a bimodal molecular weight distribution. Alternatively, two dispersing aids containing different constituent monomers or capping groups can be combined in a formulation of the invention.

An aerosol formulation preferably comprises the dispersing aid in an amount effective to stabilize the formulation relative to an identical formulation not containing the dispersing aid such that the drug does not settle, cream, or flocculate after agitation so quickly as to prevent reproducible dosing of the drug. Reproducible dosing can be achieved if the formulation retains a substantially uniform drug concentration for about two or three seconds after agitation.

The particular amount of dispersing aid that constitutes an effective amount is dependent upon the particular dispersing aid, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the dispersing aid can be present in a formulation in an amount of about 0.001 to about 1 part by weight, more preferably about 0.01 to about 0.25 parts by weight, based on 100 parts by weight of the propellant.

The formulations of the invention contain a drug in a therapeutically effective amount, that is, an amount such that the drug can be administered as an aerosol (e.g., topically or by oral or nasal inhalation) and cause its desired therapeutic effect with one dose, or less preferably several doses, from a conventional valve, e.g., a metered dose valve. "Amount" as used herein refers to quantity or to concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.02 parts by weight to about 2 parts by weight based on 100 parts by weight of the propellant.

Particularly in formulations of the invention intended for inhalation into the lungs, the drug is preferably micronized, i.e., a therapeutically effective fraction of the particles (e.g., about 90 percent or more) have a diameter of less than about 10 microns, in order to assure that the particles can be inhaled into the respiratory tract and/or lungs.

Suitable drugs for use in a formulation of the invention include any drug suitable for administration by inhalation. Therapeutic categories include antiallergics, analgesics, bronchodilators, antihistamines, antitussives, anginal preparations, antibiotics, antiinflammatories, peptides, proteins, and steroids. Particular suitable drugs include albuterol, atropine, beclomethasone, budesonide, cromolyn, epinephrine, ephedrine, fentanyl, flunisolide, formoterol, ipratropium bromide, isoproterenol, pirbuterol, prednisolone, salmeterol, and pharmaceutically acceptable salts and solvates thereof. Particularly preferred drugs include pirbuterol acetate.

An aerosol formulation of the invention also comprises a propellant. Suitable propellants include conventional chlorofluorocarbon (CFC) propellants such as mixtures of propellants 11, 12, and 114. Non-CFC propellants, particularly 1,1,1,2-tetrafluoroethane (Propellant 134a), 1,1,1,2,3,3,3-heptafluoropropane (Propellant 227), or mixtures thereof, are preferred. The propellant is preferably present in an amount sufficient to propel a plurality of doses of drug from an aerosol canister. Further components, such as conventional lubricants or surfactants, cosolvents (e.g., ethanol), and the like, can also be present in an aerosol formulation of the invention in suitable amounts readily determined by those skilled in the art.

Certain preferred dispersing aids for use in the formulations of the invention can be prepared as set forth in the Reaction Scheme below, wherein X is halogen and $R_1$, $R_2$, $R_3$, and $R_4$ are as defined above. The Reaction Scheme illustrates hydroxyacid-derived compounds. Other compounds, such as amino acid-derived compounds and mercapto acid derived compounds, can be prepared by those skilled in the art using well known methods of functional group protection and manipulation in variants of the illustrated reactions. Accordingly, those skilled in the art will recognize that the general description given below is applicable to many compounds of the invention whether or not the compounds are within the ambit of the particular preferred formulas used in the Reaction Scheme. Furthermore, many acid-derived compounds other than those illustrated in the Reaction Scheme can be prepared or otherwise obtained by those skilled in the art.

Reaction Scheme

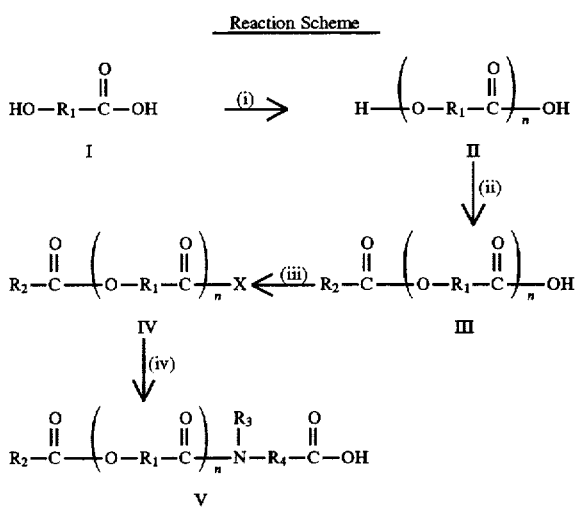

Step (i) involves condensing a hydroxyacid of Formula I. The condensation can be carried out under conventional reaction conditions such as by heating the hydroxyacid, optionally in an aprotic solvent, and preferably at a temperature sufficient to remove by distillation the water produced by the reaction (e.g., as part of an azeotropic mixture with the solvent). Chain length can be controlled by controlling the time and temperature of the reaction.

A compound of Formula II or other appropriate oligomeric or polymeric hydroxyacid can be used as a dispersing aid without further elaboration. In order to prepare certain preferred embodiments, however, further reactions can be carried out as described below.

In step (ii) a compound of Formula II can be capped at the oxy terminus by reacting with a compound containing an activated acyl group, e.g., an acid anhydride such as acetic anhydride or an acid chloride to afford a capped product of Formula III. A product of Formula III can be used as a dispersing aid without further elaboration.

In order to incorporate an amino acid residue into the compounds of a dispersing aid, the capped product of Formula III, which still possesses a carboxylic acid group, can be converted by activating the carboxylic acid and reacting with an amino acid. In Step (iii) the carboxylic acid is activated (e.g., converted to the corresponding acid halide of Formula IV) by general methods well known to those skilled in the art, such as by reacting with a carboxy activating reagent such as ethylchloroformate or a conventional chlorinating agent such as oxalyl chloride, $POCl_3$, $SOCl_2$, or the like. The amino acid group can then be incorporated in Step (iv) by reacting the acid halide of Formula IV (or an analogous activated carboxy compound) with the amino acid to afford a compound of Formula V.

Other variants of the Reaction Scheme can be readily devised in order to prepare dispersing aids other than those illustrated. For example, a polyoxyalkylene group can be incorporated as a capping group by reacting the compound of Formula IV with a polyether such as a polyethylene glycol or a block copolymer of ethylene oxide and propylene oxide. Also, the carboxy end of the compound of Formula II can be capped via esterification and/or the oxy end of the resulting compound can be reacted with a cyclic acid anhydride to incorporate an acid group. The resulting compound can then be elaborated if desired as set forth in connection with steps (iii) and (iv) of the Reaction Scheme.

An alternative method of preparing preferred embodiments involving chains derived from an α-hydroxyacid involves reacting a lactide with a nucleophile such as choline, ethyl lactate, N-acetyl hydroxyproline, tartaric acid, malic acid, propylene glycol, glycerol, N-acetyltyrosine, triethyleneglycol monomethyl ether, phosphatidyl choline, or N-acetyl ethylenediamine. The chain length of the resulting compound is readily controlled by controlling the stoichiometry of the reaction, and the product can be further elaborated by methods well known to those skilled in the art in order to provide compounds containing the various optional portions described above.

Molecular weight distribution of a product dispersing aid can be adjusted and optimized by using methods well known to those skilled in the art. Generally the dispersing aid can be fractionated by distillation or precipitation in order to provide the desired distribution. For example, low molecular weight oligomers can be readily removed by molecular distillation. With lactic acid based dispersing aids, low molecular weight oligomers (n=1, 2, or 3) can be removed by extracting with water prior to step (ii) of the Reaction Scheme.

Generally the formulations of the invention can be prepared by combining (i) the drug in an amount sufficient to provide a plurality of therapeutically effective doses; (ii) the dispersing aid; (iii) the propellant in an amount sufficient to propel a plurality of doses from an aerosol canister; and (iv) any further optional components; and dispersing the components. The components can be dispersed using a conventional mixer or homogenizer, by shaking, or by ultrasonic energy. Bulk formulation can be transferred to smaller individual aerosol vials by using valve to valve transfer methods or by using conventional cold-fill methods. It is not required that a dispersing aid used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular dispersing aids and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as those disclosed in commonly assigned copending application 08/092,001. Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, e.g., those of aluminum, glass, stainless steel, or polyethylene terephthalate, can be used to contain a formulation of the invention.

The formulations of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, or diabetes, or they can be delivered via topical (e.g., buccal) administration in order to treat, e.g., angina or local infection.

The following Examples and preparations of dispersing aids are provided to illustrate the invention. All parts and percentages are by weight unless otherwise indicated.

In the preparations of dispersing aids set forth below the structure and the average number (n) of repeating units in a chain were determined by nuclear magnetic resonance spectroscopy. The number-average relative molecular mass $M_N$ and the weight-average relative molecular mass $M_W$ were determined using gel permeation chromatography. The instrument used was a Hewlett-Packard 1090-LUSI equipped with a UV detector set at 254 nm and a refractive index detector (HP 1037A). The column set comprised 500 Angstrom columns from Jordi Associates. The samples were dissolved in tetrahydrofuran at an approximate concentration of 25 mg solids/10 mL and pressure filtered through a 0.2 micron alpha cellulose filter. An injection size of 150 μL was handled by a Hewlett-Packard 9816 computer with software supplied by Nelson Analytical. Molecular weight data are based on a calibration with polystyrene standards.

Dispersing Aid A

L-Lactic acid (200 g of a nominally 85% solution in water; 1.89 moles) and toluene (500 mL) were placed in a reaction flask equipped with a Dean-Stark trap. The reaction mixture was heated with a slow nitrogen purge for 46 hours in order to azeotropically remove water. Water (60 mL) was added and heating was continued until all the water was removed (2 hours). Acetic anhydride (289 g; 2.83 moles) was added to the mixture and heating continued for 2 hours while acetic acid was distilled off. Water (120 mL; 7.56 moles) was added and heating was continued for 2 hours. The bulk of the solvent, reactants, and side products were removed by vacuum distillation and the residual volatiles were removed under high vacuum on a rotary evaporator. The resulting crude product was dissolved in chloroform. The chloroform solution was washed twice with dilute hydrochloric acid then evaporated to provide 149.5 g of acetyl-oligo(L-lactic acid) with n=5.6, $M_N$=503 and $M_W$=729.

Dispersing Aid B

DL-Lactic acid (107 g of a nominally 85% solution in water; 1.01 moles) was placed in a reaction flask connected to an aspirator to reduce the pressure, then heated under reduced pressure to 130° C. Heating (110°–130° C.) was continued with stirring under reduced pressure for 18 hours. The aspirator was disconnected, acetic anhydride (182 g; 1.79 moles) was added and the reaction mixture was heated for 5 hours with a slow nitrogen purge while acetic acid was removed. Water (86 g; 4.76 moles) was added to the reaction and heating was continued for an additional 30 minutes. The solvent was removed by vacuum distillation followed by rotary evaporation under high vacuum. The resulting crude product was taken up in chloroform. The chloroform solution was washed 3 times with dilute hydrochloric acid then evaporated to provide acetyl-oligo(DL-lactic acid) with n=8.2, $M_N$=757 and $M_W$=982.

Dispersing Aid C

DL-Lactic acid (387 g of a nominally 85% solution in water; 3.65 moles) was placed in a reaction flask connected to an aspirator to reduce the pressure then heated (115°–150° C.) with stirring for 22 hours. The reaction mixture was cooled to room temperature then dissolved in ethyl acetate (700 mL). Hexane was added dropwise to the ethyl acetate solution until phase separation occurred after 500 mL of hexane had been added. The lower layer was combined with acetic anhydride (560 g; 5.48 moles) then heated to 95° C. and the solvents were distilled off. The reaction mixture was then stirred with heating for about 16 hours in order to remove acetic acid. Water (260 mL; 14.6 moles) was added and heating was continued for an additional 30 minutes. The volatiles were removed by distillation under aspirator vacuum followed by rotary evaporation. The crude product was extracted with chloroform. The chloroform extract was washed 3 times with dilute hydrochloric acid then evaporated to provide 196 g of acetyl-oligo(DL-lactic acid). A portion of this material was dissolved in methylene chloride. The solution was placed in a separatory funnel then diluted with hexane until phase separation occurred. The lower layer was evaporated and the resulting material was dried in a Kugelrohr apparatus at 90° C. under high vacuum for 18 hours to provide 8.0 g of acetyl-oligo(DL-lactic acid) with n=38, $M_N$=2689 and $M_W$=4183.

Dispersing Aid D

DL-Lactic acid (330 g of a nominally 85% solution in water; 3.11 moles) was placed in a reaction flask hooked to an aspirator and heated at 120° C. with stirring under reduced pressure for 22 hours. Acetic anhydride (477 g; 4.67 moles) was added and the resulting mixture was heated with stirring for 6 hours to remove acetic acid. Water (224 mL; 12.46 moles) was added and the reaction mixture was heated with stirring for an additional 30 minutes. The volatiles were removed by distillation under aspirator vacuum followed by rotary evaporation. The crude product was dissolved in ethyl acetate (400 mL). The ethyl acetate solution was diluted dropwise with hexane (430 mL) until phase separation occurred. The lower layer was separated then evaporated. The resulting residue was extracted with chloroform. The chloroform extract was washed with dilute hydrochloric acid then evaporated to provide acetyl-oligo(DL-lactic acid) with n=23, $M_N$=1146 and $M_W$=2197.

Dispersing Aid E

DL-Lactic acid (150 g of a nominally 85% solution in water; 1.42 moles) and glycolic acid (46.1 g; 0.61 moles) were combined and heated (120°–140° C.) under aspirator vacuum with stirring for 23 hours. Acetic anhydride (310 g) was added and the resulting mixture was heated with stirring for about 150 minutes to remove acetic acid. Water (146 mL) was added. The volatiles were removed by distillation under aspirator vacuum followed by rotary evaporation. The crude product was dried under high vacuum over the weekend. The crude product was then extracted with chloroform. The chloroform extract was washed 4 times with dilute hydrochloric acid then evaporated. The residue was dried under high vacuum overnight to provide 130 g of acetyl-oligo(DL-lactic-co-glycolic acid). Based on proton nuclear magnetic resonance spectroscopy, the product had a total chain length of n=12 with an average of 8.7 lactic acid units and 3.4 glycolic acid units randomly distributed therein and wherein $M_N$=578 and $M_W$=867.

Dispersing Aid F

L-Lactic acid (200 g of a nominally 85% solution in water; 1.89 moles) and toluene (1200 mL) were combined and heated for 24 hours to azeotropically remove water. Water (50 mL) was added and the reaction mixture was heated for an additional hour during which time 300 mL of solvent were removed. Acetic anhydride (289 g; 2.84 moles) was added and the reaction was heated for an additional 2 hours. The volatiles were removed by distillation under aspirator vacuum followed by rotary evaporation. The crude product was dissolved in chloroform (80 mL). The chloroform solution was washed with dilute hydrochloric acid then evaporated to provide acetyl-oligo(L-lactic acid). A portion of this material was chlorinated as described below.

Oxalyl chloride (32.7 mL; 0.375 moles) was added dropwise to a cooled (0° C.) solution containing acetyl-oligo(L-lactic acid) (40 g) in 1,2-dichloroethane (400 mL). The reaction mixture was stirred at 0° C. for an hour after the addition was completed. The reaction mixture was heated slowly to 45° C. and stirred at this temperature overnight during which time most of the 1,2-dichloroethane evaporated. Oxalyl chloride (10.9 mL) and 1,2-dichloroethane (250 mL) were added and the reaction mixture was heated at 50° C. for 1 hour. The reaction mixture was heated under aspirator vacuum to remove the volatiles. The residue was dried on a rotary evaporator and then under high vacuum to provide 33.7 g of acetyl-oligo(L-lactoyl) chloride wherein n=4.7.

The acetyl-oligo(L-lactoyl) chloride (33.7 g, 0.081 moles) was dissolved in chloroform (200 mL). Glycine (15.8 g; 0.211 moles) and sodium hydroxide (8.42 g; 0.211 moles) were dissolved in water (45 mL). The two solutions were combined and stirred at ambient temperature for 4 hours. Hydrochloric acid (25 mL) was added to adjust the pH to 2; then the reaction mixture was diluted with chloroform (80 mL). The phases were separated and the organic phase was evaporated to provide a crude product. The crude product was partitioned between chloroform and water. The chloroform layer was evaporated to provide material that by proton nuclear magnetic resonance spectroscopy was a 70:30 mixture of acetyl-oligo(L-lactoyl) N-glycine and acetyl-oligo (L-lactic acid) with n=4.0, $M_N$=491 and $M_W$=565.

Dispersing Aid G

Lactic acid (441 g; 4.90 moles) was placed in a reaction flask equipped with a distillation head. Under a nitrogen atmosphere, ethylene diamine (147 g; 2.45 moles) was slowly added with stirring to the reaction flask. During the course of the addition, the reaction mixture turned a deep orange and the temperature reached 140° C. The reaction mixture was then heated at 150° C. overnight with the water being removed by distillation. The reaction mixture was allowed to cool to 125° C. then it was poured into an aluminum pan and allowed to cool to ambient temperature, to provide 468 g of crude product. This material was recrystallized from methanol (1.9 L) to provide N,N'-1,2-ethanediylbislactamide, m.p. 188° C.

L-Lactide (12.55 g; 0.0871 mole), N,N'-1,2-ethanediylbislactamide (2.96 g, 0.0145 mole) and toluene (20 mL) were combined and gradually heated to 180° C. during which time the toluene distilled off along with a portion of the reaction mixture. Tin octoate (14 µL of 0.34M in toluene) was added and the reaction mixture was heated at 180° C. for 3 hours under nitrogen. The temperature was lowered to 130° C., acetic anhydride (4.72 g; 0.0462 mole) was added and the reaction mixture was heated at 130° C. for 150 minutes to remove acetic acid. Water (3.3 mL) was added and heating at 130° C. was continued for an additional 30 minutes. The reaction mixture was extracted with chloroform. The chloroform extract was washed twice with water then evaporated to provide 8.61 g of di[acetyl-oligo (L-lactic acid)]N,N'-ethylenediamine with n=7.0, $M_N$=1056 and $M_W$=1379.

Dispersing Aid H

L-Lactide (12.23 g; 0.0849 mole) and N,N'-1,2-ethanediylbislactamide (1.44 g; 0.00707 mole) were combined and heated to 180° C. under nitrogen. After a clear melt had formed, tin (II) octoate (13 µL of 0.34M in toluene) was added and the reaction mixture was heated at 180° C. for 3 hours. The reaction mixture was then heated at 80° C. under high vacuum to remove residual lactide. Acetic anhydride (5.22 g; 0.0511 mole) was added and the reaction mixture was heated at 130° C. for 90 minutes. Water (4 mL) was added and the reaction mixture was heated at 130° C. for an additional 30 minutes before being extracted with chloroform. The chloroform extract was washed 3 times with dilute hydrochloric acid then evaporated to provide 13.59 g of crude product. This material was dissolved in methylene chloride then diluted with hexane until phase separation occurred. The lower layer was evaporated on a rotary evaporator then the residue was dried in a Kugelrohr apparatus at 90° C. for 48 hours to provide 4.46 g of di[acetyl-oligo(L-lactic acid)]N,N'-ethylenediamine with n=11, $M_N$=1164 and $M_W$=2093.

Dispersing Aid I

L-Lactide (10.70 g; 0.0742 mole), choline chloride (3.46 g; 0.0247 mole) and toluene (20 mL) were combined then heated to distill off the toluene and remove water from the reaction mixture. Tin octoate (13 µL of 0.34M in toluene) was added and the reaction mixture was heated under nitrogen at 130° C. for 5 hours. The reaction mixture was extracted with chloroform. The chloroform extract was washed once with dilute hydrochloric acid then evaporated. The residue was dried under high vacuum at 80° C. for 16 hour. Under a nitrogen atmosphere, the dried residue was combined with acetic anhydride (7.59 g; 0.0743 mole) and heated at 130° C. for 4 hours. Water (5.5 mL) was added and the reaction mixture was heated at 130° C. for an additional 30 minutes before being extracted with chloroform. The chloroform extract was washed once with dilute hydrochloric acid then evaporated to provide 1.66 g of material which by proton nuclear magnetic resonance spectroscopy was a 80:20 mixture of acetyl-oligo(L-lactoyl)-O-choline and acetyl-oligo(L-lactic acid) with n=8.0, $M_N$=750 and $M_W$=1482.

Dispersing Aid J

Under a nitrogen atmosphere, oxalyl chloride (50 mL; 0.569 mole) was added dropwise over a period of 90 minutes to a cooled (0° C.) solution of acetyl-oligo(L-lactic acid) (140 g; 0.285 moles; n=6.3; Example 1) in 1,2-dichloroethane (350 mL). The reaction mixture was stirred at 0° C. for an additional 20 minutes then allowed to warm to ambient temperature before being heated at 45° C. for about 16 hours. The reaction mixture was heated to 80° C. to distill off solvent and excess oxalyl chloride. The residue was dried on a rotary evaporator and then under high vacuum overnight to provide 139 g of acetyl-oligo(L-lactoyl) chloride. A 10 g portion of this material was dissolved in chloroform (50 mL) then combined with ethyl alcohol (1.87 g). The reaction mixture was stirred at ambient temperature for 210 minutes then the chloroform was removed on a rotary evaporator. The residue was dried under high vacuum to provide acetyl-oligo(L-lactoyl)-O-hydroxyethane with n=6, $M_N$=700, and $M_W$=830.

Dispersing Aid K

L-Lactide (16.31 g; 0.113 mole) and propylene glycol (0.72 g; 0.0095 mole) were combined then gradually heated to 180° C. at which time tin octoate (16 µL of 0.34M in toluene) was added. The reaction mixture was heated at 180°

C. for 90 minutes. The reaction temperature was lowered to 80° C. and the reaction mixture was placed under high vacuum overnight. The vacuum was released, acetic anhydride (3.95 g) was added and the reaction mixture was heated under a nitrogen purge for 6 hours to remove acetic acid. Water (3 mL) was added and the reaction mixture was heated for an additional 30 minutes before being extracted with chloroform. The chloroform extract was washed 3 times with dilute hydrochloric acid then evaporated. The resulting residue was dried under high vacuum over a weekend to provide 14.37 g of material which by proton nuclear magnetic resonance spectroscopy was a 67:33 mixture of di[acetyl-oligo(L-lactoyl)]-O,O-1,2-hydroxypropane and acetyl-oligo(L-lactic acid) with n=8.1, $M_N$=1297 and $M_W$=1850.

Dispersing Aid L

Triethylene glycol monomethyl ether (12.01 g; 0.073 mole) was placed in a reaction flask then heated at 40° C. initially under high vacuum for 8 hours then in a closed system for 8 hours. L-Lactide (52.71 g; 0.366 mole) and tin octoate (60 µL of 0.34M in toluene) were added to the flask. The flask was placed under high vacuum at ambient temperature for 23 hours. Under a nitrogen atmosphere, the reaction mixture was heated at 180° C. with stirring for 6 hours. The reaction mixture temperature was lowered to 80° C. then the mixture was dissolved in chloroform. The chloroform solution was washed once with dilute hydrochloric acid then evaporated to provide a residue which was dried under high vacuum at 80° C. for 14 hours. The dried residue was combined with acetic anhydride (14.93 g; 0.1463 mole) and heated at 130° C. under a nitrogen atmosphere for 4 hours. Water (30 mL) was added and the reaction mixture was heated at 130° C. for an additional 30 minutes before being dissolved in chloroform. The chloroform solution was washed 3 times with dilute hydrochloric acid then evaporated to provide acetyl-oligo(L-lactoyl)-O-ethylene glycol monomethyl ether with n=11.6, $M_N$=1240, and $M_W$=1970.

Dispersing Aid M

L-Lactic acid (1.79 g of a nominally 85% solution in water; 0.0169 mole), trimethylene carbonate (10.35 g; 0.101 mole) and toluene (20 mL) were combined and heated to 180° C. After the toluene had distilled off, tin octoate (12 µL of 0.34M in toluene) was added and the reaction mixture was stirred under a nitrogen atmosphere at 180° C. for an additional 90 minutes. The reaction temperature was reduced to 80° C. then the reaction mixture was placed under vacuum overnight. The vacuum was released and acetic anhydride (15.54 g; 0.152 moles) was added. The reaction mixture was heated under a nitrogen atmosphere at 130° C. for 6 hours. Water (10.96 g) was added and the reaction mixture was heated at 130° C. for an additional 30 minutes before being extracted with chloroform. The chloroform extract was washed 3 times with dilute hydrochloric acid then evaporated. The crude product was dissolved in methylene chloride (70 mL) then washed with water. The methylene chloride layer was separated then diluted with hexane until phase separation occurred. The lower layer was evaporated and the resulting residue dried in a Kugelrohr apparatus at 90° C. for 20 hours to provide 6.42 g of a 3:1 mixture of oligotrimethylene carbonate-O-L-lactic acid and acetyl-oligo(trimethylene carbonate)-O-L-lactic acid with n=6.5, $M_N$=1664, $M_W$=3342.

EXAMPLES 1–13

Dispersing aids A–M were used to prepare suspension aerosol formulations of the invention using the following general method. Dispersing aid (25 mg) was weighed into a 4 oz (120 mL) glass aerosol vial. A continuous valve was crimped onto the vial and the vial was pressure filled with 50 g of propellant, either HFC 134a or HFC. 227, to provide a stock solution containing 0.05% by weight of dispersing aid. Micronized drug (50 mg; 30 mg in the case of triamcinolone acetonide) and glass beads (5 mL) were placed into a 15 mL glass aerosol vial. The vial was sealed with a continuous valve then pressure filled with stock solution (10 g). The vial was then shaken on a paint shaker for 10 minutes to provide an aerosol suspension formulation containing 0.05% by weight of dispersing aid and 0.5% by weight of drug (0.3% by weight of triamcinolone acetonide). The resulting suspension was stored at room temperature then shaken by hand and rated on a scale of 1 to 5. A rating of 1 indicated that agglomerates formed during shaking. A rating of 2 indicated that the suspension began flocculating immediately after shaking had ceased. A rating of 3 indicated that flocculation began 1 to 5 seconds after shaking, sufficiently long to allow reproducible dosing of the medicament. A rating of 4 indicated that flocculation began 5 to 10 seconds after shaking. A rating of 5 indicated that flocculation did not begin until at least 10 seconds after shaking had ceased. Table 1 shows the formulations that were prepared and the rating that each received. In all formulations the surfactant was present at 0.05% by weight. The drug was present at 0.5% by weight except for triamcinolone acetonide which was present at 0.3% by weight. The absence of an entry indicates that the formulation was not prepared.

TABLE 1

| Example | Dispersing aid | Pirbuterol Acetate | | Albuterol Sulfate | | Triamcinolone Acetonide | | Pirbuterol Hydrochloride | | Albuterol (Free base) | |
|---|---|---|---|---|---|---|---|---|---|---|---|
| | | 134a | 227 | 134a | 227 | 134a | 227 | 134a | 227 | 134a | 227 |
| 1 | A | 3 | 3 | | | | | 3 | | | |
| 2 | B | 3 | 5 | 3 | 5 | 3 | 3 | 3 | 3 | 3 | 4 |
| 3 | C | 3 | 5 | 3 | 5 | 3 | 3 | 3 | 3 | 3 | 5 |
| 4 | D | 3 | 5 | 3 | 5 | 2 | 3 | 2 | 2 | 3 | 5 |
| 5 | E | 3 | 3 | 3 | 3 | 3 | 3 | 3 | 3 | 3 | 3 |
| 6 | F | 3 | 5 | | | | | | | | |
| 7 | G | 3 | 5 | 3 | 3 | 3 | 4 | 3 | 3 | 3 | 4 |
| 8 | H | 2 | 2 | 3 | 3 | 3 | 5 | 3 | 3 | 3 | 5 |
| 9 | I | 3 | 4 | 3 | 4 | 2 | 2 | 2 | 2 | 2 | 3 |
| 10 | J | 2 | 3 | 2 | 3 | 2 | 3 | | | | |
| 11 | K | 3 | 5 | 3 | 5 | 3 | 5 | 2 | 2 | 3 | 4 |

TABLE 1-continued

| Example | Dispersing aid | Pirbuterol Acetate | | Albuterol Sulfate | | Triamcinolone Acetonide | | Pirbuterol Hydrochloride | | Albuterol (Free base) | |
|---|---|---|---|---|---|---|---|---|---|---|---|
| | | 134a | 227 | 134a | 227 | 134a | 227 | 134a | 227 | 134a | 227 |
| 12 | L | 3 | 3 | 3 | 3 | 3 | 3 | 3 | 3 | 3 | 3 |
| 13 | M | 2 | 2 | 2 | 2 | 2 | 2 | 2 | 2 | 2 | 2 |

The results in TABLE 1 show that the dispersing aids A–M can be used to provide aerosol formulations that are substantially readily redispersible and upon redispersion do not flocculate so quickly as to prevent reproducible dosing of the medicament. The formulation of Example 13 showed an initial rating of 3 but the formulation was somewhat unstable and after a period of several days a rating of 2 was obtained. Such instability can be avoided by judicious selection of reaction, formulation, handling, and storage conditions.

EXAMPLE 14

Using the general method of Examples 1–13, stock solutions containing 0.017% by weight, 0.024% by weight and 0.036% by weight of the Dispersing Aid A in HFC 134a were prepared. These stock solutions were used to prepare suspension aerosol formulations containing either 0.5% by weight of micronized pirbuterol acetate or 0.5% by weight of micronized pirbuterol hydrochloride. All six suspensions were given a rating of 3.

EXAMPLE 15

Dispersing Aid B (0.0374 g) was placed in an aerosol vial which was then sealed with a continuous valve. The vial was then pressure filled with 24.64 g of HFC. 134a and 45.45 g of HFC. 227 to provide a stock solution containing 0.05% by weight of surfactant. Using the general method of Examples 1–13, this stock solution was used to prepare: a suspension aerosol formulation containing 0.5% by weight of micronized pirbuterol acetate which was rated 4, a suspension aerosol formulation containing 1.0% by weight of micronized pirbuterol acetate which was rated 4, a suspension aerosol formulation containing 0.3% by weight of micronized triamcinolone acetonide which was rated 3 and a suspension aerosol formulation containing 0.5% by weight of micronized albuterol sulfate which was rated 4.

EXAMPLE 16

Using the general method of Examples 1–13, formulations were prepared using poly-L-proline as the dispersing aid. The poly-L-proline was obtained from Sigma (P-2254, lot 41H5502 with a molecular weight of 6100 as determined by low-angle laser light scattering in the static mode). The results are shown in Table 2 below.

EXAMPLE 17

Using the general method of Examples 1–13, formulations were prepared using polysarcosine as the dispersing aid. The polysarcosine was obtained from Sigma (P-2379, lot 99F4813). The results are shown in Table 2 below.

TABLE 2

| Drug | HFC | Example 16 | Example 17 |
|---|---|---|---|
| Albuterol | 134a | 2 | 3 |
| Sulfate | 227 | 5 | 4 |
| Albuterol | 134a | 3 | 3 |
| (free base) | 227 | 5 | 5 |
| Triamcinolone | 134a | 3 | 3 |
| Acetonide | 227 | 5 | 4 |
| Pirbuterol | 134a | 3 | 3 |
| Acetate | 227 | 4 | 4 |
| Pirbuterol | 134a | 5 | 3 |
| Hydrochloride | 227 | 5 | 3 |

EXAMPLE 18

Formulations using poly-L-prolines with different molecular weights were prepared as follows. Samples of poly-L-proline having three different molecular weights were obtained from Sigma (Lot 41H5502, molecular weight of 6100; Lot 87F5050, molecular weight 7800; and Lot 89F5540, molecular weight 10,100; all molecular weights as determined by Sigma). Poly-L-proline (about 16.5 mg) was weighed into a 4 oz (120 mL) glass aerosol vial. A continuous valve was crimped onto the vial and the vial was pressure filled with HFC. 227 (about 50 g) to provide a stock solution containing 0.033% by weight of the poly-L-proline. Micronized budesonide (28 mg) and glass beads (3 mL) were placed into a glass aerosol vial (10 or 15 mL). The vial was sealed with a continuous valve then pressure filled with stock solution (10 g). The vial was then shaken on a paint shaker for 15 minutes to provide an aerosol suspension formulation containing 0.28% by weight of budesonide and 0.033% by weight of poly-L-proline. The suspension prepared with the poly-L-proline having a molecular weight of 6100 was more stable than those prepared with the other two poly-L-prolines.

Dispersing Aids N and O

L-Lactic acid (228.13 g of a nominally 85% solution in water; 2.16 moles) was placed in a reaction flask equipped with a distillation head and mechanical stirrer. The reaction mixture was heated at 60° C. for 7 hours under low vacuum (aspirator) while water was removed. Acetic anhydride (219 g; 2.15 moles) was added to the mixture, followed by heating at 80° C. for 17 hours. Excess acetic anhydride and acetic acid were distilled off under low vacuum. Tetrahydrofuran/water (325 mL of 93/7; v/v) was added with stirring and heating at 60° C. for 1.5 hours. The bulk of the solvent was removed by vacuum distillation on a rotary evaporator. The resulting crude product was dissolved in chloroform (600 mL). The chloroform solution was washed twice with millipore water (150 mL) then evaporated to provide a mixture of acetyl-oligo(L-lactic acid) and acetyl-L-lactic acid. This mixture was heated at 110° C. under high vacuum on a Kugelrohr apparatus to distill acetyl-L-lactic acid (n=1, $M_N$=200, and $M_W$=200; Dispersing Aid N). The temperature was then raised to 135° C. to recover a fraction consisting of primarily acetyl-L-lactoyl-L-lactic acid with small amounts of trimer and acetyl-L-lactic acid present, (n=1.7, $M_N$=270, and $M_W$=280; Dispersing Aid O).

Dispersing Aids P, Q and R

L-Lactic acid (316.17 g of a nominally 85% solution in water; 2.99 moles) was placed in a reaction flask equipped with a distillation head and mechanical stirrer. The reaction mixture was heated at 140° C. for 4 hours under low vacuum (aspirator). Acetic anhydride (231 g; 2.25 moles) was added to the mixture, followed by heating at 80° C. for 19 hours. Excess acetic anhydride and acetic acid were then distilled off under low vacuum. Tetrahydrofuran/water (325 mL of 92/8; v/v) was added with stirring and heating at 40° C. for 1.0 hours. The bulk of the solvent was removed by vacuum distillation on a rotary evaporator. The resulting crude product was dissolved in chloroform (725 mL). A portion of this chloroform solution (300 mL) was continuously extracted with distilled water (estimated volume of water was 3 liters), then evaporated to provide acetyl-oligo(L-lactic acid) with n=4.3, $M_N$=460 and $M_W$=590 (Dispersing Aid Q). Dispersing Aid Q was free of acetyl lactic acid, and substantially free of acetyl lactoyl lactic acid. The remaining chloroform solution was washed twice with millipore water (250 mL) then evaporated to provide acetyl-oligo(L-lactic acid). This mixture was heated at 110° C. under high vacuum on a Kugelrohr apparatus to remove lactide then heated at 135° C. to distill acetyl-oligo(L-lactic acid) with n=3.2, $M_N$=320 and $M_W$=330 primarily consisting of dimer and trimer (Dispersing Aid P). The residue was acetyl-oligo(L-lactic acid) with n=5.79, $M_N$=630, and $M_W$=730 (Dispersing Aid R). Dispersing Aid R was free of acetyl-L-lactic acid, acetyl-L-lactoyl-L-lactic acid and contained substantially reduced levels of trimer.

EXAMPLES 19–23

Using the methods of Examples 1–13, formulations using Dispersing Aids N–O were prepared and rated. Table 3 shows the formulations that were prepared and the rating that each received. In all formulations the dispersing aid was present at 0.05% by weight. The drug was present at 0.5% by weight except for triamcinolone acetonide which was present at 0.3% by weight. The absence of an entry indicates that the formulation was not prepared.

vacuum (7 mmHg) and the temperature was raised to 140° C. to distill off water. After 4 hrs the reaction was cooled to 80° C. and acetic anhydride (200 mL) was added. The solution was stirred at 80° C. overnight under a slow nitrogen purge. After 12 or more hours the remaining acetic anhydride and acetic acid were removed under vacuum. After the acetic acid/acetic anhydride distillation was complete, 180 mL of tetrahydrofuran/water (85/15; v/v) was added with stirring and the flask temperature was allowed to drop to 60° C. After 15 min the reaction mixture was transferred to a round bottom flask and the tetrahydrofuran was removed under vacuum on a rotary evaporator. Chloroform (600 mL) was added and the resulting solution was extracted twice with millipore water (200 mL) in a separatory funnel and then dried with $MgSO_4$. The mixture was filtered through a "d" fritted glass funnel and the solvent distilled from the oligomer by rotary evaporation. Final traces of solvents were removed under high vacuum (0.4 mmHg) on a Kugelrohr apparatus at 90° C. to provide acetyl-oligo(L-lactic acid) with n=4.35, $M_N$=530, and $M_W$=670.

Dispersing Aids T, U and V

DL-lactic acid (300 g of a nominally 85% solution; 2.38 moles) was placed in a 1 L 3-neck flask equipped with a mechanical stirrer, distillation head, and a thermometer. The reaction mixture was heated at 140° C. for 4 hours under low vacuum (aspirator, 7 mmHg). Acetic anhydride (270 g; 2.65 moles) was added to the mixture, followed by heating at 80° C. for 19 hours. Excess acetic anhydride and acetic acid were then distilled off under low vacuum. Tetrahydrofuran/water (200 mL of 85/15; v/v) was added with stirring and the flask temperature was allowed to drop to 60° C. After 15 min the reaction mixture was transferred to a round bottom flask and the tetrahydrofuran was removed under vacuum on a rotary evaporator. Chloroform (600 mL) was added and the resulting solution was extracted twice with millipore water (200 mL) in a separatory funnel and then dried with $MgSO_4$. The mixture was filtered through a "d" fritted glass funnel and the solvent distilled from the oligomer by rotary evaporation. Final traces of solvents were removed under high vacuum (0.4 mmHg) on a Kugelrohr apparatus at 90° C. to yield acetyl oligo(DL-lactic acid). The product was then distilled at 0.4 mmHg at 156° C. on a falling film molecular still to remove oligomers with n≦2 resulting in acetyl oligo(DL-lactic acid) n=7.69, $M_N$=627, and $M_W$=882 (Dispersing Aid T) which was substantially free of dimer

TABLE 3

| Example | Dispersing aid | Pirbuterol Acetate | | Albuterol Sulfate | | Triamcinolone Acetonide | | Pirbuterol Hydrochloride | | Albuterol (Free base) | |
|---|---|---|---|---|---|---|---|---|---|---|---|
| | | 134a | 227 | 134a | 227 | 134a | 227 | 134a | 227 | 134a | 227 |
| 19 | N | 2 | 2 | 2 | 2 | 2 | 2 | 2 | 2 | 2 | 2 |
| 20 | O | 2 | 2 | 2 | 2 | 2 | 2 | 2 | 2 | 2 | 2 |
| 21 | P | 2 | 3 | 2 | 3 | 2 | 3 | 2 | 2 | 2 | 2 |
| 22 | Q | 3 | 5 | 3 | 5 | 3 | 3 | 3 | 3 | 2 | 4 |
| 23 | R | 4 | 5 | 4 | 5 | 3 | 4 | 2 | | 3 | 5 |

Dispersing Aid S

L-lactide (200 g; 1.39 moles) and water (200 mL; millipore) were placed in a 1 L 3-neck flask equipped with a mechanical stirrer, distillation head, and a thermometer. The reaction mixture was warmed to 80° C. and stirred under nitrogen overnight. The flask was then placed under and monoester. The temperature was then raised to 190° C. and oligomers with n=3 to 6 were distilled off. The resulting acetyl-oligo(DL-lactic acid) had values of n=3.8, $M_N$=418, and $M_W$=433, with the following distribution 25.2% of n=3, 40% of n=4, 22.6% of n=5, and 9.9% of n=6 as determined by GPC (Dispersing Aid U). The residue consisted of acetyl-oligo(DL-lactic acid) with n=9.38, $M_N$=827, and $M_W$=1072 (Dispersing Aid V). Dispersing Aid V contained less than 1% of material with n=1 or 2; less than 2.3% of material with n=3, and less than 6.14% of material with n=4.

Dispersing Aid W

DL-2-Hydroxycaproic acid (1.00 g, 0.0076 moles) was placed in a mini reaction flask (5 mL) equipped with a distillation head and magnetic spin vane. The flask was heated at 110° C. for 24 hours under low vacuum (aspirator). Acetic anhydride (1 g; 0.0098 moles) was added to the oligomer, followed by heating at 110° C. for 18 hours. Excess acetic anhydride and acetic acid were distilled off under low vacuum. Tetrahydrofuran/water (1 mL of 85/15; v/v) was added with stirring and heating at 60° C. for 0.5 hours. The bulk of the solvent was removed by vacuum distillation on a rotary evaporator. The resulting crude product was dissolved in chloroform (10 mL). The chloroform solution was washed twice with millipore water (5 mL) and then dried with $MgSO_4$. The mixture was filtered through a "d" fritted glass funnel and the solvent distilled from the oligomer by rotary evaporation. Final traces of solvents were removed under high vacuum (0.4 mmHg) on a Kugelrohr apparatus at 120° C. to provide acetyl-oligo(D, L-hydroxycaproic acid) with n=7.4, $M_N$=830, and $M_W$=1214.

Dispersing Aid X

DL-2-Hydroxycaproic acid (1.00 g, 0.0076 moles), and L-lactic acid (4.5 g of a nominally 85% solution in water; 0.043 moles) were placed in a reaction flask equipped with a distillation head and mechanical stirrer. The flask was heated at 110° C. for 6 hours under low vacuum (aspirator) while water was removed. The temperature was then raised to 140° C. for 6 hours. Acetic anhydride (5.16 g; 0.0506 moles) was added to the oligomer, followed by heating at 80° C. for 14 hours. Excess acetic anhydride and acetic acid were distilled off under low vacuum. Tetrahydrofuran/water (15 mL of 85/15; v/v) was added with stirring and heating at 60° C. for 0.5 hours. The bulk of the solvent was removed by vacuum distillation on a rotary evaporator. The resulting crude product was dissolved in chloroform (20 mL). The chloroform solution was washed twice with millipore water (5 mL) and then dried with $MgSO_4$. The mixture was filtered through a "d" fritted glass funnel and the solvent distilled from the oligomer by rotary evaporation. Final traces of solvents were removed under high vacuum (0.4 mmHg) on a Kugelrohr apparatus at 120° C. to provide acetyl-oligo(D, L-2-hydroxycaproic-co-L-Lactic acid) with n=7.5 for lactic acid and 1.4 for hydroxycaproic acid, $M_N$=763, and $M_W$=1044.

Dispersing Aid Y

L-Lactic acid (4.03 g of a nominally 85% solution in water; 0.038 moles) was placed in a reaction flask equipped with a distillation head and mechanical stirrer. The reaction mixture was heated at 140° C. for 2 hours under low vacuum (aspirator). Trimethylene carbonate (15.52 g, 0.1522 moles) and 50 µl of a tin octanoate solution (0.33M in toluene) were added and the mixture was allowed to react an additional 4 hours. Acetic anhydride (19.4 g; 0.19 moles) was added to the mixture, followed by heating at 80° C. for 18 hours. Excess acetic anhydride and acetic acid were then distilled off under low vacuum. Tetrahydrofuran/water (50 mL of 93/7; v/v) was added with stirring and heating at 40° C. for 0.25 hours. The bulk of the solvent was removed by vacuum distillation on a rotary evaporator. The resulting crude product was dissolved in chloroform (75 mL) and washed twice with millipore water (50 mL) and then dried with $MgSO_4$. The mixture was filtered through a "d" fritted glass funnel and the solvent distilled from the oligomer by rotary evaporation. Final traces of solvents were removed under high vacuum (0.4 mmHg) on a Kugelrohr apparatus at 120° C. to provide acetyl-oligo(L-lactic acid-co-trimethylene carbonate). Trimethylene carbonate n=15.9, lactic acid n=3, $M_N$=2037, $M_W$=3442.

Dispersing Aid Z

L-Lactide (85.07 g; 0.945 moles) and water (100 mL; millipore) were placed in a 1 L 3-neck flask equipped with a mechanical stirrer, distillation head, and a thermometer. The reaction mixture was warmed to 80° C. and stirred under nitrogen overnight. The flask was then placed under vacuum (aspirator, 7 mmHg) and the temperature was raised to 140° C. to distill off water. After 2 hrs trimethylene carbonate (8.51 g, 0.083 moles) was added. Two hours later a second portion of trimethylene carbonate (8.52 g, 0.083 moles) was added and the reaction was allowed to proceed for 3 more hours. The reaction was cooled to 80° C. and 120 mL of acetic anhydride was added. The solution was stirred at 80° C. overnight under a slow nitrogen purge. After 18 hours the remaining acetic anhydride and acetic acid were removed under vacuum. After the acetic acid and acetic anhydride distillation was complete, 180 mL of tetrahydrofuran/water (85/15; v/v) was added with stirring and the flask temperature was allowed to drop to 60° C. After 15 min the reaction mixture was transferred to a round bottom flask and the tetrahydrofuran was removed under vacuum on a rotary evaporator. Chloroform (300 mL) was added and the resulting solution was extracted twice with 150 mL of millipore water in a separatory funnel and then dried with $MgSO_4$. The mixture was filtered through a "d" fritted glass funnel and the solvent distilled from the oligomer by rotary evaporation. Final traces of solvents were removed under high vacuum (0.4 mmHg) on a Kugelrohr apparatus at 90° C. to yield acetyl-oligo(L-lactic acid-co-trimethylene carbonate) with trimethylene carbonate n=1.6, lactic acid n=7.6, $M_N$=974, and $M_W$=1684.

Dispersing Aid AA

Thiolactic acid (4.16 g, 0.039 moles), L-lactic acid (23.5 g of a nominally 85% solution in water; 0.22 moles) and 50 µl of a tin octanoate solution (0.33M in toluene) were placed in a reaction flask equipped with a distillation head and mechanical stirrer. The flask was heated at 110° C. for 1 hour under low vacuum (aspirator) while water was removed. The temperature was then raised to 140° C. for 9 hours. Acetic anhydride (30 g; 0.29 moles) was added to the oligomer, followed by heating at 80° C. for 14 hours. Excess acetic anhydride and acetic acid were distilled off under low vacuum. Tetrahydrofuran/water (15 mL of 85/15; v/v) was added with stirring and heating at 60° C. for 0.25 hours. The bulk of the solvent was removed by vacuum distillation on a rotary evaporator. The resulting crude product was dissolved in chloroform (40 mL). The chloroform solution was washed twice with millipore water (25 mL), dried with $MgSO_4$, filtered and the solvent distilled from the oligomer by rotary evaporation. Final traces of solvents were removed under high vacuum (0.4 mmHg) on a Kugelrohr apparatus at 90° C. to yield acetyl-oligo(D,L-thiolactic-co-L-lactic acid), n=4.6, $M_N$=473, $M_W$=695.

Dispersing Aid BB

L-Lactide (8.72 g; 0.061 moles), p-dioxanone (1.34 g, 0.013 moles) and water (10 mL; millipore) were placed in a 50 mL 3-neck flask equipped with a mechanical stirrer, distillation head, and a thermometer. The reaction mixture was warmed to 80° C. and stirred under nitrogen overnight. The flask was then placed under vacuum (aspirator, 7 mmHg) and the temperature was raised to 110° C. to distill off water. After 1 hour, 200 μl of tin octanoate (0.33M in toluene) was added and the reaction proceeded for 16 hours. The flask was cooled to 80° C. and 10 mL of acetic anhydride was added. The solution was stirred at 80° C. overnight under a slow nitrogen purge. After 8 hours the remaining acetic anhydride and acetic acid were removed under vacuum. After the acetic acid and acetic anhydride distillation was complete, 25 mL of tetrahydrofuran/water (85/15; v/v) was added with stirring and the flask temperature was allowed to drop to 60° C. After 15 min the reaction mixture was transferred to a round bottom flask and the tetrahydrofuran was removed under vacuum on a rotary evaporator. Chloroform (50 mL) was added and the resulting solution was extracted twice with 20 mL of millipore water in a separatory funnel and then dried with $MgSO_4$. The mixture was filtered through a "d" fritted glass funnel and the solvent distilled from the oligomer by rotary evaporation. Final traces of solvents and monomer were removed under high vacuum (0.4 mmHg) on a Kugelrohr apparatus at 90° C. to yield acetyl-oligo(dioxanone-co-L-lactic acid) with dioxanone n=0.6, lactic acid n=7.5.

Dispersing Aid CC

P-dioxanone (5.29 g, 0.0518 moles) and L-lactic acid (5.48 g of a nominally 85% solution in water; 0.052 moles) were placed in a reaction flask equipped with a distillation head and stir bar. The reaction mixture was warmed to 100° C. and stirred under nitrogen for 2 hours. The temperature was raised to 140° C., 200 μl of tin octanoate (0.33M in toluene) was added and the reaction proceeded for 8 hours. During this time half of the monomers distilled off. The reaction was cooled to 80° C. and 10 mL of acetic anhydride was added. The solution was stirred at 80° C. overnight under nitrogen. The remaining acetic anhydride and acetic acid were removed under vacuum. Tetrahydrofuran/water (28 mL; 25/75; v/v) was added with stirring. After 10 min the tetrahydrofuran was removed under vacuum on a rotary evaporator. Chloroform (5×20 mL) was added and the resulting solution was extracted one time with 20 mL of millipore water in a separatory funnel. The solvent was distilled from the oligomer by rotary evaporation. Final traces of solvents were removed under high vacuum (0.4 mmHg) on a Kugelrohr apparatus at 110° C. to yield acetyl-oligo(dioxanone-co-L-lactic acid) with dioxanone n=1.9, lactic acid n=3.6, $M_N$=998, $M_W$=1922.

EXAMPLES 24–34

Using the methods of Examples 1–13, formulations using Dispersing Aids S–CC, were prepared and rated. Table 4 shows the formulations that were prepared and the rating that each received. In all formulations the dispersing aid was present at 0.05% by weight. The drug was present at 0.3% by weight.

TABLE 4

| Ex | Dispersing Aid | Albuterol Sulfate | | Pirbuterol Acetate | | Triamcinolone Acetonide | |
|----|----|-----|-----|-----|-----|-----|-----|
|    |    | 134a | 227 | 134a | 227 | 134a | 227 |
| 24 | S  | 5 | 5 | 2 | 2 | 2 | 2 |
| 25 | T  | 5 | 5 | 3 | 5 | 2 | 2 |
| 26 | U  | 5 | 5 | 2 | 4 | 2 | 2 |
| 27 | V  | 4 | 5 | 3 | 5 | 2 | 2 |
| 28 | W  | 3 | 4 | 2 | 3 | 2 | 2 |
| 29 | X  | 4 | 5 | 3 | 5 | 3 | 4 |
| 30 | Y  | 2 | 2 | 2 | 4 | 2 | 2 |
| 31 | Z  | 3 | 5 | 2 | 5 | 2 | 4 |
| 32 | AA | 5 | 5 | 2 | 2 | 2 | 2 |
| 33 | BB | 3 | 5 | 2 | 4 | 2 | 4 |
| 34 | CC | 2 | 2 | 2 | 4 | 2 | 2 |

Dispersing Aid DD

Dispersing Aid S was further distilled on a falling film molecular distillation unit at 110° C. to remove low molecular weight oligomers to provide acetyl-oligo (L-lactic acid) with n=5.8, $M_N$=656, and $M_W$=756, free of acetyl-L-lactic acid and acetyl-L-lactoyl L-lactic acid.

Dispersing Aid EE

L-lactide (200 g; 1.38 moles) and water (200 mL; millipore) were placed in a 1 L 3-neck flask equipped with a mechanical stirrer, distillation head, and a thermometer. The reaction mixture was warmed to 80° C. and stirred under nitrogen overnight. The flask was then placed under vacuum (aspirator, 7 mmHg) and the temperature was raised to 140° C. to distill off water. After 6 hrs the reaction was cooled to 80° C. and 200 mL of acetic anhydride was added. The solution was stirred at 80° C. overnight under a slow nitrogen purge. After 12 or more hours the remaining acetic anhydride and acetic acid were removed under vacuum. After the acetic acid and acetic anhydride distillation was complete, 180 mL of tetrahydrofuran/water (85/15; v/v) was added with stirring and the flask temperature was allowed to drop to 60° C. After 15 min the reaction mixture was transferred to a round bottom flask and the tetrahydrofuran was removed under vacuum on a rotary evaporator. Chloroform (600 mL) was added and the resulting solution was extracted twice with 200 mL of millipore water in a separatory funnel and then dried with $MgSO_4$. The mixture was filtered through a "d" fritted glass funnel and the solvent distilled from the oligomer by rotary evaporation. Final traces of solvents and monomer were removed under high vacuum (0.4 mmHg) on a Kugelrohr apparatus at 90° C. Further distillation on a falling film molecular distillation unit at 110° C. removed low molecular weight oligomers to provide acetyl-oligo (L-lactic acid) with n=7.56, $M_N$=776, and $M_W$=994, substantially free of acetyl-L-lactic acid and acetyl-L-lactoyl-L-lactic acid.

Dispersing Aids FF and GG

L-Lactide (200 g; 1.38 moles) and water (200 mL; millipore) were placed in a 1 L 3-neck flask equipped with a mechanical stirrer, distillation head, and a thermometer. The reaction mixture was warmed to 80° C. and stirred under nitrogen overnight. The flask was then placed under vacuum (aspirator, 7 mmHg) and the temperature was raised to 140° C. to distill off water. After 8 hrs the reaction was cooled to 80° C. and 600 mL of chloroform was added with stirring. The organic layer was extracted twice with 200 mL of water in a separatory funnel and then dried with MgSO$_4$. The mixture was filtered through a "d" fritted glass funnel and the solvent distilled from the oligomer by rotary evaporation. The oligomer was transferred to a clean 1000 mL 3 neck flask equipped as described above and 200 mL of acetic anhydride was added. The solution was stirred at 80° C. overnight under nitrogen. After 12 or more hours the remaining acetic anhydride and acetic acid were removed under vacuum. After the acetic acid and acetic anhydride distillation was complete, 180 mL of tetrahydrofuran/water (85/15; v/v) was added with stirring and the flask temperature was allowed to drop to 60° C. After 15 min the reaction mixture was transferred to a round bottom flask and the tetrahydrofuran was removed under vacuum on a rotary evaporator. Chloroform (600 mL) was added and the resulting solution was extracted twice with 200 mL of millipore water in a separatory funnel and then dried with MgSO$_4$. The mixture was filtered through a "d" fritted glass funnel and the solvent distilled from the oligomer by rotary evaporation. Final traces of solvents and monomer were removed under high vacuum (0.4 mmHg) on a Kugelrohr apparatus at 90° C. Distillation on a falling film molecular distillation unit at 110° C. removed low molecular weight oligomers to provide acetyl-oligo-(L-lactic acid) with n=9.9, $M_N$=740, and $M_W$=1350 (Dispersing Aid FF). Dispersing Aid FF was free of acetyl-L-lactic acid and acetyl-L-lactoyl-L-lactic acid. Further distillation on a falling film molecular distillation unit at 110° C. removed low molecular weight oligomers to provide acetyl-oligo-(L-lactic acid) with n=11.0, $M_N$=1090, and $M_W$=1520 (Dispersing Aid GG). Dispersing Aid GG was free of acetyl-L-lactic acid, acetyl-L-lactoyl L-lactic acid, and substantially free of trimer.

EXAMPLES 35–38

Using the general methods of Examples 1–13 (except that the formulations were agitated without glass beads using ultrasound instead of by shaking in the presence of glass beads) formulations using Dispersing Aids DD - GG were prepared and rated. Table 5 shows the formulations that were prepared and the rating that each received. In all formulations the dispersing aid was present at 0.05% by weight. The drug was present at 0.03% by weight.

TABLE 5

| Example Number | Dispersing Aid | Budesonide 134a | Budesonide 227 | Albuterol Sulfate 134a | Albuterol Sulfate 227 | Pirbuterol Acetate 134a | Pirbuterol Acetate 227 | Disodium Cromoglycate 134a | Disodium Cromoglycate 227 |
|---|---|---|---|---|---|---|---|---|---|
| 35 | DD | 2 | 3 | 2 | 4 | 2 | 3 | 5 | 5 |
| 36 | EE | 2 | 3 | 2 | 4 | 2 | 3 | 5 | 5 |
| 37 | FF | 2 | 3 | 3 | 4 | 2 | 4 | 5 | 5 |
| 38 | GG | 2 | 3 | 3 | 4 | 2 | 3 | 5 | 5 |

We claim:

1. A metered dose inhaler containing a medicinal aerosol formulation, the formulation comprising:
   (i) a dispersing aid comprising a compound comprising a chain of units derived from a precursor selected from the group consisting of a hydroxyacid, an amino acid, a mercapto acid, and a combination of any two or more of the foregoing;
   (ii) a propellant; and
   (iii) a therapeutically effective amount of a particulate drug, wherein the formulation is substantially readily redispersible and upon redispersion does not flocculate, cream, or settle so quickly as to prevent reproducible dosing of the drug.

2. A metered dose inhaler according to claim 1, wherein the chain of the formulation is capped on at least one end by a group that contains no hydrogen atoms capable of hydrogen bonding.

3. A metered dose inhaler according to claim 1, wherein the chain of the formulation is bonded at least one end to a moiety that contains an ionic group.

4. A metered dose inhaler according to claim 1, wherein the chain of the formulation is bonded at least one end to a moiety that contains a group that contains one or more hydrogen atoms capable of hydrogen bonding.

5. A metered dose inhaler according to claim 1, wherein the dispersing aid comprises a chain comprising units derived from one or more hydroxyacids.

6. A metered dose inhaler according to claim 1, wherein the chain of the formulation comprises units derived from a precursor selected from the group consisting of glycolic acid, trimethylene carbonate, hydroxybutyric acid, p-dixanone, and lactic acid.

7. A metered dose inhaler according to claim 1, wherein the chain of the formulation comprises units derived from L-lactic acid.

8. A metered dose inhaler according to claim 1, wherein the dispersing aid comprises a chain comprising units derived from one or more amino acids.

9. A metered dose inhaler according to claim 1, wherein the dispersing aid comprises a chain comprising units derived from one or more mercapto acids.

10. A metered dose inhaler according to claim 1, wherein the formulation comprises a mixture of a first dispersing aid and a second dispersing aid.

11. A metered dose inhaler containing a medicinal aerosol formulation, the formulation comprising:
   (i) a dispersing aid comprising a compound comprising a chain of units of the formula

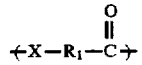

wherein each $R_1$ is an independently selected organic moiety that links the -x-group to the carbonyl group, and X is —O—, —S—, or catenary nitrogen;

(ii) a propellant; and
   (iii) a therapeutically effect amount of a particulate drug; wherein the formulation is substantially readily redispersible and upon redispersion does not flocculate, settle, or cream so quickly as to prevent reproducible dosing of the drug.

12. A metered dose inhaler according to claim 11, wherein the chain of the formulation contains less than about 100 of said units.

13. A metered dose inhaler according to claim 11, wherein the chain of the formulation contains between about 3 and about 70 of said units.

14. A metered dose inhaler according to claim 11, wherein the chain of the formulation contains between about 3 and about 14 of said units.

15. A metered dose inhaler according to claim 11, wherein $R_1$ is straight chain, branched chain, or cyclic alkylene or alkenylene, optionally containing carbonyl, oxy, thio, or catenary nitrogen, arylene or arylene substituted by non-nucleophilic or non-hydrogen donor hydrogen bonding functional groups, or a combination of such arylene, alkenylene, and alkylene groups.

16. A metered dose inhaler according to claim 11, wherein —X— is catenary fully substituted nitrogen wherein the substituent is a group that is free of nucleophilic or hydrogen-donor hydrogen bonding functional groups.

17. A metered dose inhaler according to claim 11, wherein the carbonyl end of the chain is bonded to an α-amino acid residue of the formula

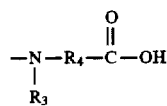

wherein $R_3$ is hydrogen and $R_4$ is straight chain, branched chain, or cyclic alkylene containing one catenary carbon atom and a total of one to about 12 carbon atoms, optionally substituted by one or more of lower alkoxy, lower alkylthio, carboxy, mercapto, hydroxy, phenyl, hydroxyphenyl, indolyl, guanidinyl, carbamido, imidazolyl, or acylamino, or wherein $R_3$ and $R_4$ together form a butane-1,1,4-triyl group optionally substituted by hydroxy.

18. A metered dose inhaler according to claim 17, wherein the carbonyl end of the chain is bonded to a group derived from taurine.

19. A metered dose inhaler according to claim 17, wherein the chain comprises units of the formula —OCH(CH$_3$)C(O)—.

* * * * *